US007582576B2

(12) United States Patent
Snijder et al.

(10) Patent No.: US 7,582,576 B2
(45) Date of Patent: Sep. 1, 2009

(54) SURGICAL SOFT TISSUE MESH

(75) Inventors: Carina Sacha Snijder, Sittard (NL); Leonard Josef Arnold Nielaba, Eygelshoven (NL)

(73) Assignee: DSM IP Assets B.V., Heerlen (NL)

( * ) Notice: Subject to any disclaimer, the term of this patent is extended or adjusted under 35 U.S.C. 154(b) by 254 days.

(21) Appl. No.: 10/537,895

(22) PCT Filed: Dec. 11, 2003

(86) PCT No.: PCT/NL03/00881

§ 371 (c)(1),
(2), (4) Date: Jul. 19, 2005

(87) PCT Pub. No.: WO2004/052421

PCT Pub. Date: Jun. 24, 2004

(65) Prior Publication Data

US 2006/0014459 A1    Jan. 19, 2006

(30) Foreign Application Priority Data

Dec. 11, 2002   (EP)   ................... 02102732

(51) Int. Cl.
*D03D 9/00* (2006.01)
(52) U.S. Cl. ............ 442/1; 442/2; 442/4; 442/43; 442/46; 442/49; 442/50; 442/51; 442/58; 442/123; 442/308; 442/309; 442/311; 428/373; 428/374; 428/397; 606/151
(58) Field of Classification Search .......... 442/1, 442/2, 4, 43, 46, 49, 50, 51, 58, 123, 308, 442/309, 311; 428/373, 374, 397; 606/151
See application file for complete search history.

(56) References Cited

U.S. PATENT DOCUMENTS

| 3,054,406 | A |   | 9/1962  | Mesh |       |
|-----------|---|---|---------|------|-------|
| 3,124,136 | A |   | 3/1964  | Usher |      |
| 6,042,592 | A |   | 3/2000  | Schmitt |    |
| 6,090,116 | A | * | 7/2000  | D'Aversa et al. | 606/151 |
| 6,669,706 | B2| * | 12/2003 | Schmitt et al. | 606/151 |

FOREIGN PATENT DOCUMENTS

| EP | 0 205 960 | 12/1986 |
| EP | 0 561 108 |  9/1993 |

OTHER PUBLICATIONS

International Search Report.

* cited by examiner

*Primary Examiner*—Ula C Ruddock
(74) *Attorney, Agent, or Firm*—Nixon & Vanderhye P.C.

(57) ABSTRACT

The invention relates to a soft and flexible surgical soft tissue mesh comprising polyethylene yarns, wherein the polyethylene yarns have a tensile strength of more than 1.0 Gpa and consist of a polyethylene with a relative viscosity of more than 5 dl/g. A further aspect of the invention is a method of producing a soft and flexible surgical soft tissue mesh comprising polyethylene yarns, wherein yarns are applied that comprise filaments made by: a) spinning at least one filament from a solution of polyethylene with a relative viscosity of more than 5 dl/g in a solvent; b) cooling the filament obtained to form a gel filament; c) removing at least partly the solvent from the gel filament; and d) drawing the filament in at least one drawing step before, during or after removing solvent.

10 Claims, No Drawings

SURGICAL SOFT TISSUE MESH

This application is the US national phase of international application PCT/NL2003/000881 filed 11 Dec. 2003 which designated the U.S. and claims benefit of EP 02102732.1, dated 11 Dec. 2002, the entire content of which is hereby incorporated by reference.

The present invention relates to a surgical mesh and, more particularly, to a soft and flexible surgical soft tissue mesh.

Using surgical mesh for the repair and restoration of living tissue is well known. For example, in U.S. Pat. No. 6,042,592 a surgical mesh is described, which is used to support and/or reinforce a damaged or weakened portion of the body. U.S. Pat. No. 6,042,592 further describes that a mesh must additionally be sufficiently porous to allow for growth of tissue through the graft after implantation. A healing tissue generally grows through porous openings in the implanted mesh, thereby assimilating the mesh and adding structural integrity to the tissue.

U.S. Pat. No. 3,054,406 discloses another example of a surgical mesh used for repair and restoration of living tissue. The surgical mesh described therein may be woven from either monofilament or multifilament polyethylene yarns. The mesh has limited pliability when formed of monofilament yarns, and may be prone to harboring of infectious matter when formed of multifilament yarns.

A surgical mesh has been extremely useful in the field of repairing soft tissue such as during a hernia repair operation. Groin herniorrhaphy is among the oldest and most common surgical procedures performed. Unfortunately, the average operative result is beset by a period of discomfort with resultant disability. Techniques have been developed, such as laparoscopic herniorrhaphy, with the intent to reduce morbidity and recurrence rates. Most trials, however, have noted only a moderate improvement in the pain and disability associated with the procedure. Further, the added cost of equipment, the need for general anesthesia, and the additional operating room time required for laparoscopic herniorrhaphy indicates that this procedure is less than ideal. There continues to be a need for a procedure that can effectively address all the considerations of cost, disability, and hernia recurrence for patients with an inguinal hernia.

While the placement of a prosthetic mesh in the properitoneal space is currently performed with either a laparoscopic or an open technique, it is desirable to perform the procedure through even less invasive means. One such means contemplated involves the use of needles to deliver the mesh into the peritoneal cavity. Delivery of mesh by means of a needle, however, has heretofore hardly been possible in part due to the unavailability of a mesh which is thin enough to be passed through the cannula of a needle, yet of sufficient tenacity and flexibility to adequately serve its intended purpose.

There is therefore a need for a surgical soft tissue mesh, which can be made having a thickness that allows the mesh to be rolled or folded and thereafter inserted into the cannula of a needle for deployment in the body and which exhibits both the soft and pliable characteristics of a mesh produced from multifilament yarns and the infection resistance of a mesh produced from monofilament yarns. In order to provide a mesh with a low thickness, the yarns of which the mesh is made should have a high tenacity or strength. However yarns with a high tenacity generally have a too low flexibility for surgical meshes.

It is the aim of the invention to provide a mesh, which combines flexibility with a sufficient tenacity to obtain a thinner mesh than the known meshes.

According to the invention this is obtained by a mesh comprising polyethylene yarns having a tensile strength of more than 1.0 GPa and consisting of a polyethylene with a relative viscosity of more than 5 dl/g.

Herewith a mesh can be obtained which is both thin and flexible enough for the surgical use mentioned above.

A surgical mesh can be produced by knitting, weaving, braiding, or otherwise forming a plurality of yarns into a mesh. Preferably the mesh of the invention is knitted.

The mesh comprises polyethylene yarns having a tensile strength of more than 1.0 GPa, preferably more than 1.5, 2.0 or even more than 3.0 GPa. Tensile strength, also simple strength, is determined on multifilament yarns as specified in ASTM D885M, using a nominal gauge length of the fibre of 500 mm, a crosshead speed of 50%/min and Instron 2714 clamps, type Fibre Grip D5618C. The polyethylene yarns in the mesh according to the invention consist of a polyethylene with a relative viscosity of more than 5 dl/g, as measured on a solution of polyethylene in decalin with a concentration of 0.05% at 135° C. according to ASTM D 4020. Preferably the relative viscosity of the polyethylene is more than 10 dl/g. An advantage of a mesh comprising a yarn made from polyethylene with a relative viscosity of more than 10 dl/g is the high fatigue strength of such a mesh. The polyethylene may further comprise minor amounts of the usual additives, like catalyst residues or stabilizers.

The thickness of the yarn may vary between wide ranges. A suitable thickness for the yarns in the mesh of the invention, however, is between 10 and 500 denier in view of the flexibility of the mesh.

A mesh can be produced with monofilament or multifilament yarns. Surgical mesh formed of monofilament yarn provides satisfactory reinforcement ability, but is generally stiff and has limited pliability. In contrast surgical mesh formed of multifilament yarn is soft and flexible in comparison to mesh formed of monofilament yarn. However, mesh formed of multifilament yarn may tend to harbour infectious matter such as bacteria. Particularly, the small void areas or interstitial spaces between the filaments of multifilament yarns may promote the breeding of such bacteria. To date, surgeons typically prefer the monofilament design because of its improved resistance to harbouring of infectious matter. As a result of this choice, surgeons must forego the advantages associated with multifilament yarns.

In a special embodiment of the invention the polyethylene yarns are sheath and core yarns, having a weight ratio between the sheath and the core of below 5:1. In this sheath and core yarn the core is formed by filaments that show no or only little adhesion to each other, that is most filaments can still be separated, e.g. when the yarn is cut lengthwise or the sheath is removed. The sheath of the yarn is a substantially non-porous layer, which layer may for example have been formed from outer filaments of a precursor yarn molten together as a result of heat exposure. The precursor yarn can be a continuous multifilament yarn, but also a spun yarn made from staple fibres. Preferably the precursor yarn is a multifilament yarn. The sheath being substantially non-porous is understood to mean that no or hardly any pores or void areas can be seen, e.g. with a microscope, such that bacteria or other microorganisms will not find a breeding place. The relative thickness of the sheath should be below a certain value, such that the sheath and core yarn combines the advantages of a flexible, yet high tenacity multifilament or spun yarn with that of a monofilament being less prone to harbouring of infectious matter. Such a yarn further shows less fraying and improved resistance to ravelling. Preferably, the weight ratio between the sheath and the core is below 3:1, or even below 2:1, since this enhances flexibility, especially for thicker yarns.

The flexibility of the mesh is generally higher if a thinner yarn is applied. Very thin yarn, however, may be more difficult to handle. In a preferred embodiment, the mesh is produced from a construction, like a braid or laid cord, comprising at least two sheath and core yarns of low denier. The advantage thereof is a high flexibility, and still low risk of harbouring of infectious matter in view of the larger dimensions of interstitial spaces between the sheath and core yarns compared with filaments of a multifilament yarn.

In another preferred embodiment of the present invention, a medicinal drug (e.g. an antibiotic) has been incorporated into the yarns.

The invention further relates to a method of producing a soft and flexible surgical soft tissue mesh comprising polyethylene yarns, wherein the yarns comprise filaments made by:
a) spinning at least one filament from a solution of polyethylene with a relative viscosity of more than 5 dl/g in a first solvent;
b) cooling the filament obtained to form a solvent-containing gel filament;
c) removing at least partly the solvent from the gel filament; and
d) drawing the filament in at least one drawing step before, during or after removing solvent, to result in a tensile strength of more than 1.0 GPa.

Such a spinning process is generally referred to as a gel spinning process. Gel spinning of polyethylene with a relative viscosity of more than 5 dl/g (ultra high molecular weight polyethylene; UHMwPE) has been described in various publications, including EP 0205960 A, EP 0213208 A1, U.S. Pat. No. 4,413,110, WO 01/73173 A1, and Advanced Fiber Spinning Technology, Ed. T. Nakajima, Woodhead Publ. Ltd (1994), ISBN 1-855-73182-7, and references cited therein. Suitable solvents for this spinning process are known, and include for example paraffins, mineral oil, kerosene or decalin. Spinning solvent can be removed by evaporation, extraction, or by a combination of evaporation and extraction routes.

In a preferred embodiment, the solvent is substantially completely removed, that is to a level below the content that is allowable for the envisaged application. Preferably, the yarn obtained contains less than 800 ppm of solvent, more preferably less than 500, 250, or even less than 100 ppm.

The invention further relates to a preferred method, further comprising a step wherein the yarns are subjected to a heat treatment, optionally in the presence of a second solvent for polyethylene, in which step a modified yarn comprising a sheath and a core is formed, with a weight ratio between sheath and core of below 5:1, preferably below 3:1, or even below 2:1. In this process the yarns may be as spun untwisted filaments or in the form of braided, twisted or intermingled bundles of filaments, or in the form of a spun yarn.

The conditions, like temperature and residence time of the process according to the preferred method of the invention are selected to be high, respectively long enough to soften the filaments and allow them to combine at least at the surface of the yarn such that a sheath is formed, which sheath is substantially non-porous. Conditions useful for the surface combining process include a temperature or series of oven temperatures within the melting point range of the filament polymer that allows for forming a sheath and core structure during the exposure period. The temperature at which the preferred process is carried out is preferably within the range from about 150° C. up to about 157° C. for gel spun polyethylene yarns exhibiting a relaxed melting range of 138° to about 162° C. at a 20° C./minute scan rate and having a relative viscosity of more than 5 dl/g. Residence times during which the yarn is exposed to the oven temperature are within the range from about 6 seconds to about 150 seconds. In a special embodiment of the invention, part of the drawing of the filaments may be done simultaneously with the forming of a sheath and core structure. In view of the increase in length of yarn, longer ovens may be needed, which would result in longer residence times than indicated above. To prevent that the yarn is exposed to too much heat, the temperature profile applied can be adjusted, e.g. by applying a lower initial temperature, for example in the range 135-150° C. The weight ratio between sheath and core can be adjusted by increasing or decreasing the oven temperature, increasing or decreasing the residence time, or by applying a pressure to the surface of the yarns. The skilled man can find favourable settings by routine experimentation.

Optionally a second solvent can be applied to the surface of the yarn, to enhance the process of making a sheath and core yarn. Such second solvent may include mineral oil (e.g. heat transfer grade mineral oil with an average molecular weight of 250-700 g/mol), paraffin oil, and vegetable oil (e.g., coconut oil), or any other solvent for polyethylene such as decalin, or toluene. Contact between the thread or yarn and the second solvent can be performed under ambient conditions (e.g., 20°-25° C.) or under elevated temperature conditions (e.g. up to about 100-150° C. or higher). This second solvent, for example mineral oil, is thought to act as a plasticiser, and enhances the efficiency of the process; permitting the process for making the sheath and core yarn to be performed at lower temperatures. After forming the sheath structure, the yarn may be subjected to an additional heat treatment at lower temperatures, which treatment will result in substantially complete removal of the second solvent, or at least to below concentrations allowed as maximum for the envisaged application of the yarn. Preferably, the yarn obtained contains less than 800 ppm of solvent, more preferably less than 500, 250, or even less than 100 ppm.

Optionally the first and the second solvent are the same.

The invention also relates to a method of producing a soft and flexible surgical soft tissue mesh wherein the method further comprises a step of incorporating a medical drug into the yarns.

This step of incorporating a drug can be done by adding the medical drug to the first solvent wherein the polyethylene is dissolved. Another way to incorporate a medical drug into the yarns is to add the medical drug to the second solvent, but also other routes are possible.

In order to obtain a more stable mesh structure the yarns of the mesh can be optionally subjected to a heat-setting step. This can be done by heating the mesh under constant strain at a temperature between the melting temperature of the polyethylene and a temperature that is not more than 20 degrees below the melting temperature. During this heat-treatment, also relaxation processes may occur. The desirability of this step is dependent on the structure of the mesh; and appears less effective for a knitted mesh.

The invention further relates to a method of repairing damaged soft tissue of a patient's body, comprising a step wherein a surgical mesh according to the invention is implanted in said body to reinforce said damaged tissue. In a special embodiment of the method according to the invention, the surgical mesh is implanted using a hollow needle.

The invention claimed is:

1. Soft and flexible surgical soft tissue mesh comprising polyethylene yarns, wherein
   the polyethylene yarns
   (i) have a tensile strength of more than 1.0 GPa, determined as specified in ASTM D885M using a nominal gauge length of a fiber of 500 mm and a crosshead speed of 50%/min, and
   (ii) include multiple filaments in a sheath region thereof and multiple filaments in a core region thereof, wherein
   the multiple filaments in the sheath and core regions thereof consist of polyethylene with a relative viscosity of more than 5 dl/g as measured on a solution of polyethylene in decalin with a concentration of 0.05% at 135° C. according to ASTM D 4020, and wherein
   a weight ratio between the multiple filaments in the sheath region and the multiple filaments in the core region is below 5:1, and wherein
   the multiple filaments in the core region show substantially no adhesion to each other, and wherein
   the multiple filaments in the sheath region form a substantially non-porous layer around the multiple filaments in the core region.

2. Mesh according to claim 1, wherein the mesh is knitted.

3. Mesh according to claim 1, wherein the yarns have a weight ratio between the multiple filaments of the sheath region and the multiple filaments of the core region of below 3:1.

4. Mesh according to claim 1, wherein at least one of the yarns comprises a medical drug.

5. Mesh according to claim 1, wherein the multiple filaments of the sheath region melt-adhered to one another.

6. A polyethylene yarn comprising:
   multiple sheath filaments in a sheath region of the yarn and multiple core filaments in a core region of the yarn, wherein each of the sheath and core filaments consist of polyethylene with a relative viscosity of more than 5 dl/g as measured on a solution of polyethylene in decalin with a concentration of 0.05% at 135° C. according to ASTM D 4020, wherein
   the polyethylene sheath filaments and polyethylene core filaments are present in the yarn in a weight ratio of sheath filaments to core filaments of below 5:1, and wherein
   the core filaments show substantially no adhesion to each other and the sheath filaments form a substantially non-porous layer around the core filaments, and wherein
   the yarn has a tensile strength of more than 1.0 GPa, determined as specified in ASTM D885M using a nominal gauge length of a fiber of 500 mm and a crosshead speed of 50%/mm.

7. The yarn according to claim 6, wherein the weight ratio of the sheath filaments to the core filaments is below 3:1.

8. The yarn according to claim 6, wherein the weight ratio of the sheath filaments to the core filaments is below 2:1.

9. The yarn according to claim 6, wherein the sheath filaments are melt-adhered to one another.

10. A surgical mesh which includes a yarn according to claim 6.

* * * * *